United States Patent [19]

Hanifin, Jr. et al.

[11] 4,254,047

[45] Mar. 3, 1981

[54] SUBSTITUTED PHENYL-2-CYANO-2-THIOALKENOIC ACID ESTERS

[75] Inventors: John W. Hanifin, Jr., Suffern; David N. Ridge, Upper Grandview, both of N.Y.

[73] Assignee: American Cyanamid Company, Stamford, Conn.

[21] Appl. No.: 104,527

[22] Filed: Dec. 17, 1979

[51] Int. Cl.³ .................. A61K 31/275; C07C 153/11
[52] U.S. Cl. ............................ 260/455 R; 260/438.1; 424/301; 548/248
[58] Field of Search .................. 260/455 R, 438.1; 424/301

[56] References Cited

U.S. PATENT DOCUMENTS

| 4,061,767 | 12/1977 | Ertel et al. | 424/282 |
| 4,173,650 | 11/1979 | Hanifin, Jr. et al. | 424/304 |

*Primary Examiner*—Dolph H. Torrence
*Attorney, Agent, or Firm*—Edward A. Conroy, Jr.

[57] ABSTRACT

Substituted phenyl-2-cyano-2-thioalkenoic acid esters which are useful as anti-inflammatory agents and as inhibitors of the progressive joint deterioration characteristic of arthritic disease.

17 Claims, No Drawings

SUBSTITUTED PHENYL-2-CYANO-2-THIOALKENOIC ACID ESTERS

DESCRIPTION OF THE INVENTION

This invention is concerned with compounds of the formula:

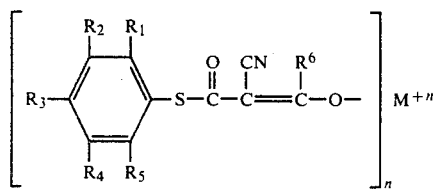

wherein $R_1$, $R_2$, $R_3$, $R_4$ and $R_5$ are each selected from the group comprising hydrogen, halogen, lower alkyl ($C_1$–$C_4$), lower alkoxy ($C_1$–$C_4$), trifluoromethyl and trichloromethyl, $R_6$ is lower alkyl ($C_1$–$C_4$); M is hydrogen or a pharmaceutically acceptable cation; and n is an integer one, two or three.

The useful pharmaceutically acceptable salts of the compounds of the above structural formula wherein M is hydrogen are those with pharmacologically acceptable metal cations, ammonium, amine cations or quaternary ammonium cations. Preferred metal cations are those derived from the alkali metals, e.g. lithium, sodium and potassium, and from the alkaline earth metals, e.g. magnesium and calcium, although cationic forms of other metals, e.g. aluminum, iron, zinc and in particular copper are within the scope of this invention.

Pharmacologically acceptable amine cations and those derived from primary, secondary or tertiary amines such as mono-, di- or trimethylamine, ethylamine, dibutylamine, triisopropylamine, N-methylhexylamine, decylamine, dodecylamine, allylamine, crotylamine, cyclopentylamine, dicyclohexylamine, mono- or dibenzylamine, α- or β-phenylethylamine, ethylenediamine, diethylenetriamine, and aryliphatic amines containing up to and including 18 carbon atmos, as well as heterocyclic amines, e.g. piperidine, morpholine, pyrrolidine, piperazine and lower alkyl derivatives thereof, e.g. 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizng or hydrophilic groups, e.g. mono-, di- or triethanolamine, ethyldiethanolamine, N-butylethanolamine, 2-amino-1-butanol, 2-amino-2-ethyl-1, 3-propanediol, 2-amino-2-methyl-1-propanol, tris (hydroxymethyl)aminomethane, N-phenylethanolamine, N-(p-tert-amylphenyl)diethanolamine, galactamine, N-methylglucamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium and the like.

The compounds of the present invention may be prepared according to the following Flowchart A.

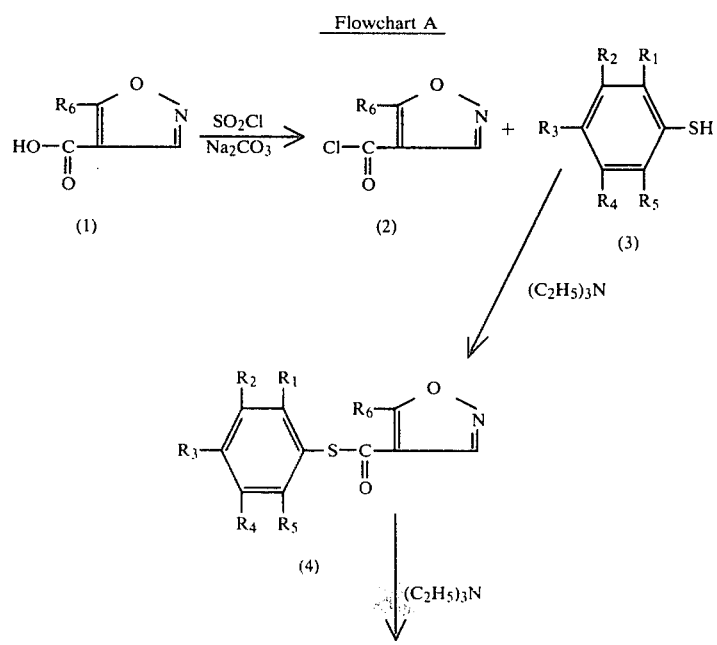

Flowchart A

Flowchart A

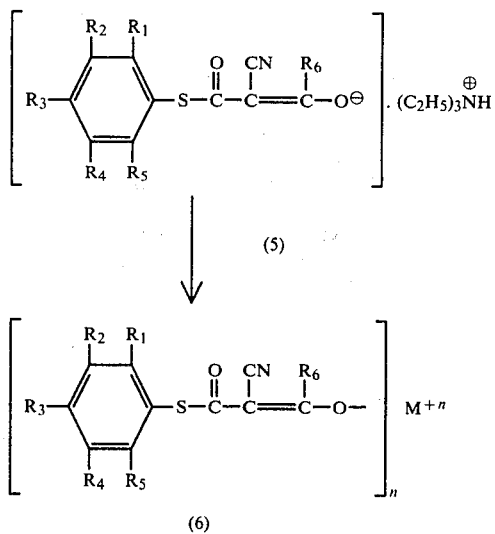

In accordance with Flowchart A thionyl chloride and sodium carbonate in chloroform are used to convert a 5-alkylisoxazole 4-carboxylic acid (1) to the corresponding 5-alkylisoxazole carbonyl chloride (2) by heating for several hours. The compound (2) is then reacted with a substituted thiophenol (3) and one molar equivalent of triethylamine in ether at reduced temperature for several hours. The resulting alkylthio isoxazolecarboxylic acid-S-phenyl ester (4) is extracted in methylenechloride and crystallized with hexane at reduced temperature. The isoxazole (4) is treated with triethylamine in ether for several hours giving the 2-cyano-3-hydroxythio alkenoic acid-5-phenyl ester triethylamine salt (5) which is then acidified in aqueous solution with hydrochloric acid to provide (6) where $R_1$, $R_2$, $R_3$, $R_4$, $R_5$, $R_6$ and M are as described above.

DETAILED DESCRIPTION OF THE INVENTION

The compounds of the present invention have been found to be highly useful for meliorating inflammation and inhibiting joint deterioration in mammals when administered in amounts ranging from about one milligram to about 250 mg. per kilogram of body weight per day. A preferred dosage regimen for optimum results would be from about 5 mg. to about 100 mg. per kilogram of body weight per day, and such dosage units are employed that a total of from about 0.35 gram to about 7.0 grams of the active ingredient for a subject of about 70 kg. of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. A decided practical advantage of this invention is that the active ingredient may be administered in any convenient manner such as by the oral, intravenous, intramuscular, topical or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10 to 10.0% by weight, it is preferred that the amount of active compound employed be from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, phenyl mercuric nitrate, benzalkonium chloride, phenethyl alcohol, p-chlorophenyl-α-glycerol ether, methyl and propyl parabens, and thimerosal. As a practical matter it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

For intramuscular injection, the preferred concentration of active compound is 0.25 to 0.50 mg./ml. of the finished compositions. The compounds of this invention are equally adapted to intravenous administration when diluted with water or diluents employed in intravenous therapy such as isotonic glucose in appropriate quantities. For intravenous use, initial concentrations down to about 0.05 to 0.25 mg./ml. of active compound are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active ingredient in such therapeutically useful compositions is such that a suitable dosage will be obtained. Preferred compositions or preparations according to the present invention are prepared so that an oral dosage unit form contains between about 50 and 250 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

Those compounds of the invention which have anti-inflammatory activity have had their activity confirmed in the synovium-cartilage test which is a modification of the method described by Dumonde, D. C. and Glynn, L. E., The Production of Arthritis in Rabbits by an Immunological Reaction to Fibrin, Brit. J. Exp. Pathol., 43, 373 (1962).

Synovium-cartilage Test

Male, New Zealand rabbits, weighing 1.6-3.0 kg. were used. The rabbits were housed in individual cages and given food and water ad libitum. The rabbits were sensitized to bovine serum albumin (BSA) by injection of 20 mg./kg. BSA in complete Freund's adjuvant. The emulsion was injected subcutaneously into multiple sites on the back. Total injection volume equaled one mg./kg. of body weight. Between 18 and 21 days following immunization, the rabbits were challenged with an intraarticular injection of 5 mg. BSA into the right knee joint. Unanesthetized animals were restrained on their backs, and a 20-gauge, one-inch needle, with a 5 ml. syringe, was introduced into the joint and synovial fluid aspirated to determine that the synovium had been penetrated. The needle was then left in place for injection of the antigen. A 0.5 ml. portion of 10 mg./ml. BSA in sterile saline was injected into the synovial sac. The rabbits received an additional five intraarticular injections of 5 mg. BSA into the right knee at intervals of 12-16 days. Following the sixth injection the rabbits were sacrificed by an intracardiac injection of 5 ml. of a saturated solution of potassium chloride. The right knee was shaved. A longitudinal incision was made over the patellar ligament and the skin reflected under sterile conditions. The patellar ligament was cut tranversely and reflected. Facia and capsular tissue were trimmed from the lateral and medial aspects of the knee exposing the synovial membrane. The membrane was grasped with forceps, stretched laterally and then excised in a single piece on each side of the knee. The infrapatellar fat pad was removed and the joint space widened by cutting the anterior attachments of the menisci and severing the collateral cruciate ligaments. The femur and tibia were then separated and the menisci excised along with sufficient amounts of synovial tissue from the popliteal area adhereing to the menisci. The tissue were immediately placed in a sterile Petri dish containing tissue culture medium composed of MEM (Earle's salts) without sodium bicarbonate, with 25 mM Hepes buffer, pH adjusted to 7.34-7.37, and antibiotics (streptomycin nd neomycin, 100 units/ml.). Ten percent normal rabbit serum (NRS) was added. The tissues were rinsed three times in fresh medium plus 10% NRS, then cut into pieces of 20-30 mg.

Articular cartilage was obtained from the knees of normal, young rabbits, weighing 1.0 to 1.5 kg. The knees were shaved, the rabbits sacrificed and the joint exposed as described above. Synovial tissue and the infrapatellar fat pad were removed. Ligaments were severed and the menisci excised. Femur and tibia were then separated and articular cartilage was cut from supracondylar lines, patellar surface and femoral condyles. Due to curvature of the bone, these pieces were not more than 6-7 mg. each. No cartilage was taken from the tibia. The cartilage was placed in a sterile Petri dish containing tissue culture medium plus 10% NRS and rinsed three times with fresh medium +10% NRS. The cartilage was then cut into 1-2 mg. pieces and stored at $-70°$ C.

A 10 mg. portion of the test compound was dissolved or suspended in absolute ethanol. Ten $\mu$l. were then transferred to the complete tissue culture medium. The final concentration of test compound was then 10 mcg./ml. and the vehicle 0.1%.

Tissue culture medium was added to 12×75 mm clear plastic culture tubes containing one piece of normal articular cartilage. A piece of arthritic synovial tissue was then added to all tubes except those tubes in which cartilage was incubated alone. All tubes were then incubated at 37° C. for 48 hours with constant rotation in a roller drum at 0.2 rpm. After 48 hours the cartilage was removed, hydrolyzed and assayed for hexoseamine and hydroxyproline. Hexoseamine to hydroxyproline ratios were calculated for the three groups:
1. Cartilage alone
2. Cartilage+synovium
3. Cartilage+synovium+test compound.

Cartilage hexoseamine decreases when it is cultured in the presence of synovium but remains constant when cultured alone. Hydroxyproline remains constant in all groups and the amount assayed is a measure of the size of the incubated cartilage. Therefore, the hexoseamine/hydroxyproline ratio decreases in the cartilage+synovium group relative to the cartilage alone group. The decrease is approximately 50%.

If a compound prevents the decrease in the hexoseamine/hydroxyproline ratio by greater than 50% it is retested. A compound is considered active if it averages greater than 50% suppression of break down in three separate tests.

The compound 2-cyano-3-hydroxythiocrotonic acid-S-phenyl ester is active when tested by the above procedure having a mean percent inhibition of 105.77% based on three tests.

EXAMPLE 1

2-Cyano-3-hydroxythiocrotonic acid-S-phenyl ester

A 72 ml. portion of thionyl chloride is added dropwise to a mixture of 70.24 g. of 5-methylisoxazole-4-carboxylic acid [H. Yasuda, Yakugaku Zasshi, 79, 836–838 (1959); C. A. 53, 21885d] and 64.44 g. of sodium carbonate in 250 ml. of chloroform. The mixture is heated gently on a steam bath for 4 hours, then the solid is filtered and the filtrate is evaporated to an oil. This oil is distilled at 4.5 mm. and the material boiling at 68°–70° C. is collected, giving 65.23 g. of 5-methylisoxazole-4-carbonyl chloride.

A mixture of 10.27 ml. (11.02 g.) of thiophenol and 11.15 ml. (14.6 g.) of 5-methylisoxazole-4-carbonyl chloride in 50 ml. of ether is cooled in an ice bath. A 14 ml. portion of triethylamine is diluted to 50 ml. with ether and added dropwise. The mixture is stirred for 2 hours and the solid is filtered and washed with ether. The filtrate is evaporated to an oil which crystallizes, is taken up in methylene chloride and filtered through diatomaceous earth. The filtrate is concentrated on a steam bath with the addition of hexanes, giving an oil. Cooling crystallizes this oil giving 16.65 g. of 5-methylthio-4-isoxazolecarboxylic acid-S-phenyl ester as a white crystalline solid.

An 8 ml. portion of triethylamine in 50 ml. of ether is cooled in an ice bath and a mixture of 11.91 g. of 5-methylthio-4-isoxazolecarboxylic acid-S-phenyl ester in 60 ml. of ether is added dropwise. The reaction is stirred overnight and the solid is filtered, giving 15.15 g. of 2-cyano-3-hydroxythiocrotonic acid-S-phenyl ester triethylamine salts as a white crystalline solid. A 10.17 g. portion of this triethylamine salt is dissolved in 100 ml. of water and 2.64 ml. of concentrated hydrochloric acid is added, giving an oil which solidifies. The solid is filtered and dried, giving the desired product, m.p. 106°–108° C.

EXAMPLE 2

2-Cyano-3-hydroxythiocrotonic acid-S-(p-chlorophenyl)ester

A 14.46 g. portion of p-chlorothiophenol and 11.15 ml. (14.6 g.) of 5-methylisoxazole-4-carbonyl chloride in 50 ml. of ether is cooled in an ice bath and a solution of 14 ml. of triethylamine in 50 ml. of ether is added dropwise. The mixture is stirred for 3 hours and then diluted with ether. The solid is filtered and washed with ether. The combined filtrate and washing is evaporated to a solid which is taken up in methylene chloride, filtered and evaporated on a steam bath with the addition of hexanes giving an oil which crystallizes on cooling, giving 5-methylthio-4-isoxazolecarboxylic acid-S-(p-chlorophenyl)ester as a white crystalline solid.

A 17.60 g. portion of the above isoxazole is slurried with 100 ml. of ether and cooled in an ice bath. A solution of 15 ml. of triethylamine in 50 ml. of ether is added dropwise and the reaction is stirred overnight. The solid is filtered and dried, giving 23.61 g. of 2-cyano-3-hydroxythiocrotonic acid-S-(p-chlorophenyl)ester triethylamine salt as a white crystalline solid.

A 9.17 g. portion of the above salt is taken up in 50 ml. of water and filtered. A 2.4 ml. portion of concentrated hydrochloric acid is added to the filtrate and the reaction is stirred for 2 hours. The solid is filtered and dried giving 6.10 g. of the desired product as a white crystalline solid, m.p. 91°–94° C.

Following the general procedure of Examples 1 and 2, other representative compounds of this invention, such as those found in Table I, may be made.

TABLE I

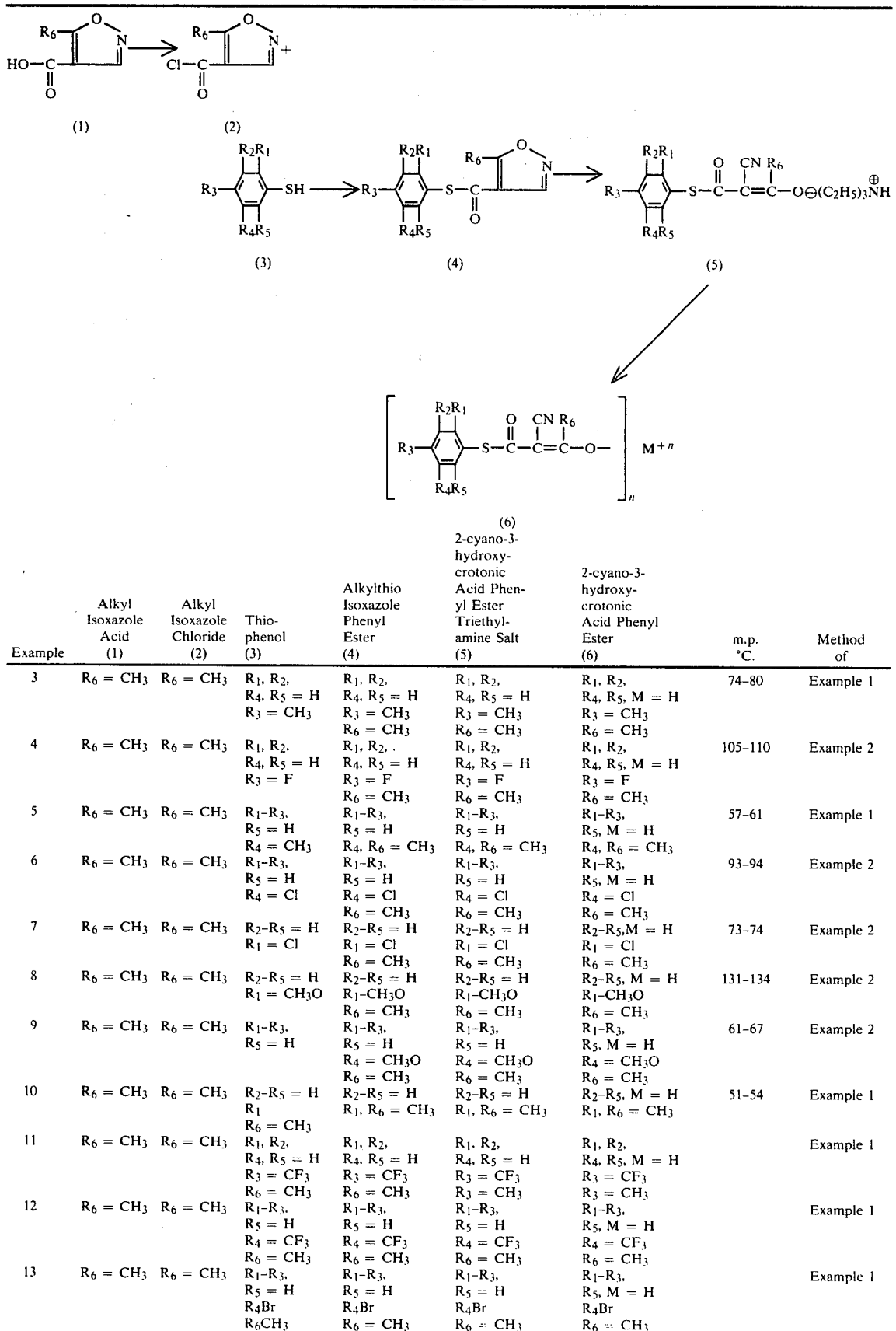

| Example | Alkyl Isoxazole Acid (1) | Alkyl Isoxazole Chloride (2) | Thio-phenol (3) | Alkylthio Isoxazole Phenyl Ester (4) | 2-cyano-3-hydroxy-crotonic Acid Phenyl Ester Triethyl-amine Salt (5) | 2-cyano-3-hydroxy-crotonic Acid Phenyl Ester (6) | m.p. °C. | Method of |
|---|---|---|---|---|---|---|---|---|
| 3 | $R_6 = CH_3$ | $R_6 = CH_3$ | $R_1, R_2, R_4, R_5 = H$ $R_3 = CH_3$ | $R_1, R_2, R_4, R_5 = H$ $R_3 = CH_3$ $R_6 = CH_3$ | $R_1, R_2, R_4, R_5 = H$ $R_3 = CH_3$ $R_6 = CH_3$ | $R_1, R_2, R_4, R_5, M = H$ $R_3 = CH_3$ $R_6 = CH_3$ | 74–80 | Example 1 |
| 4 | $R_6 = CH_3$ | $R_6 = CH_3$ | $R_1, R_2, R_4, R_5 = H$ $R_3 = F$ | $R_1, R_2, R_4, R_5 = H$ $R_3 = F$ $R_6 = CH_3$ | $R_1, R_2, R_4, R_5 = H$ $R_3 = F$ $R_6 = CH_3$ | $R_1, R_2, R_4, R_5, M = H$ $R_3 = F$ $R_6 = CH_3$ | 105–110 | Example 2 |
| 5 | $R_6 = CH_3$ | $R_6 = CH_3$ | $R_1-R_3, R_5 = H$ $R_4 = CH_3$ | $R_1-R_3, R_5 = H$ $R_4, R_6 = CH_3$ | $R_1-R_3, R_5 = H$ $R_4, R_6 = CH_3$ | $R_1-R_3, R_5, M = H$ $R_4, R_6 = CH_3$ | 57–61 | Example 1 |
| 6 | $R_6 = CH_3$ | $R_6 = CH_3$ | $R_1-R_3, R_5 = H$ $R_4 = Cl$ | $R_1-R_3, R_5 = H$ $R_4 = Cl$ $R_6 = CH_3$ | $R_1-R_3, R_5 = H$ $R_4 = Cl$ $R_6 = CH_3$ | $R_1-R_3, R_5, M = H$ $R_4 = Cl$ $R_6 = CH_3$ | 93–94 | Example 2 |
| 7 | $R_6 = CH_3$ | $R_6 = CH_3$ | $R_2-R_5 = H$ $R_1 = Cl$ | $R_2-R_5 = H$ $R_1 = Cl$ $R_6 = CH_3$ | $R_2-R_5 = H$ $R_1 = Cl$ $R_6 = CH_3$ | $R_2-R_5, M = H$ $R_1 = Cl$ $R_6 = CH_3$ | 73–74 | Example 2 |
| 8 | $R_6 = CH_3$ | $R_6 = CH_3$ | $R_2-R_5 = H$ $R_1 = CH_3O$ | $R_2-R_5 = H$ $R_1 = CH_3O$ $R_6 = CH_3$ | $R_2-R_5 = H$ $R_1 = CH_3O$ $R_6 = CH_3$ | $R_2-R_5, M = H$ $R_1 = CH_3O$ $R_6 = CH_3$ | 131–134 | Example 2 |
| 9 | $R_6 = CH_3$ | $R_6 = CH_3$ | $R_1-R_3, R_5 = H$ $R_4 = CH_3O$ | $R_1-R_3, R_5 = H$ $R_4 = CH_3O$ $R_6 = CH_3$ | $R_1-R_3, R_5 = H$ $R_4 = CH_3O$ $R_6 = CH_3$ | $R_1-R_3, R_5, M = H$ $R_4 = CH_3O$ $R_6 = CH_3$ | 61–67 | Example 2 |
| 10 | $R_6 = CH_3$ | $R_6 = CH_3$ | $R_2-R_5 = H$ $R_1$ $R_6 = CH_3$ | $R_2-R_5 = H$ $R_1, R_6 = CH_3$ | $R_2-R_5 = H$ $R_1, R_6 = CH_3$ | $R_2-R_5, M = H$ $R_1, R_6 = CH_3$ | 51–54 | Example 1 |
| 11 | $R_6 = CH_3$ | $R_6 = CH_3$ | $R_1, R_2, R_4, R_5 = H$ $R_3 = CF_3$ $R_6 = CH_3$ | $R_1, R_2, R_4, R_5 = H$ $R_3 = CF_3$ $R_6 = CH_3$ | $R_1, R_2, R_4, R_5 = H$ $R_3 = CF_3$ $R_3 = CH_3$ | $R_1, R_2, R_4, R_5, M = H$ $R_3 = CF_3$ $R_3 = CH_3$ | | Example 1 |
| 12 | $R_6 = CH_3$ | $R_6 = CH_3$ | $R_1-R_3, R_5 = H$ $R_4 = CF_3$ $R_6 = CH_3$ | $R_1-R_3, R_5 = H$ $R_4 = CF_3$ $R_6 = CH_3$ | $R_1-R_3, R_5 = H$ $R_4 = CF_3$ $R_6 = CH_3$ | $R_1-R_3, R_5, M = H$ $R_4 = CF_3$ $R_6 = CH_3$ | | Example 1 |
| 13 | $R_6 = CH_3$ | $R_6 = CH_3$ | $R_1-R_3, R_5 = H$ $R_4Br$ $R_6CH_3$ | $R_1-R_3, R_5 = H$ $R_4Br$ $R_6 = CH_3$ | $R_1-R_3, R_5 = H$ $R_4Br$ $R_6 = CH_3$ | $R_1-R_3, R_5, M = H$ $R_4Br$ $R_6 = CH_3$ | | Example 1 |

We claim:

1. A compound selected from those of the formula:

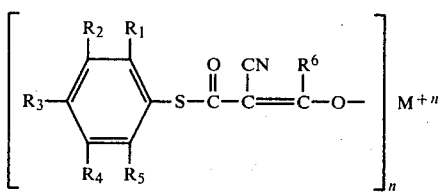

wherein $R_1$, $R_2$, $R_3$, $R_4$ and $R_5$ are each selected from the group comprising hydrogen, halogen, lower alkyl ($C_1$–$C_4$), lower alkoxy ($C_1$–$C_4$), trifluoromethyl and trichloromethyl; $R_6$ is lower alkyl ($C_1$–$C_4$); M is hydrogen or a pharmaceutically acceptable cation; and n is an integer one, two or three.

2. The compound according to claim 1; 2-cyano-3-hydroxythiocrotonic acid-S-phenyl ester.

3. The compound according to claim 1; 2-cyano-3-hydroxythiocrotonic acid-S-(p-chlorophenyl)ester.

4. The compound according to claim 1; 2-cyano-3-hydroxythiocrotonic acid-S-p-tolyl ester.

5. The compound according to claim 1; 2-cyano-3-hydroxythiocrotonic acid-S-p-fluorophenyl ester.

6. The compound according to claim 1; 2-cyano-3-hydroxythiocrotonic acid-S-m-tolyl ester.

7. The compound according to claim 1; 2-cyano-3-hydroxythiocrotonic acid-S-(m-chlorophenyl) ester.

8. The compound according to claim 1; 2-cyano-3-hydroxythiocrotonic acid-S-(o-chlorophenyl) ester.

9. The compound according to claim 1; 2-cyano-3-hydroxythiocrotonic acid-S-(o-methoxyphenyl) ester.

10. The compound according to claim 1; 2-cyano-3-hydroxythiocrotonic acid-S-(m-methoxyphenyl) ester.

11. The compound according to claim 1; 2-cyano-3-hydroxythiocrotonic acid-S-o-tolyl ester.

12. The compound according to claim 1; 2-cyano-3-hydroxythiocrotonic acid-S-(p-trifluoromethylphenyl)ester.

13. The compound according to claim 1; 2-cyano-3-hydroxythiocrotonic acid-S-(m-trifluoromethylphenyl)ester.

14. The compound according to claim 1; 2-cyano-3-hydroxythiocrotonic acid-S-(m-bromophenyl)ester.

15. The compound according to claim 1; 2-cyano-3-hydroxythiocrotonic acid-S-phenyl ester sodium salt.

16. The compound according to claim 1; 2-cyano-3-hydroxythiocrotonic acid-S-(p-chlorophenyl ester triethylamine salt.

17. The compound according to claim 1; 2-cyano-3-hydroxythiocrotonic acid-S-p-tolyl ester cupric salt.

* * * * *